US009120891B2

(12) United States Patent
Lee et al.

(10) Patent No.: US 9,120,891 B2
(45) Date of Patent: Sep. 1, 2015

(54) METHOD FOR PREPARING POLYLACTATE AND COPOLYMER THEREOF USING A MUTANT MICROORGANISM WITH ENHANCED POLYLACTATE, AND THE COPOLYMER PRODUCING CAPABILITY THEREOF

(75) Inventors: Sang Yup Lee, Daejeon (KR); Yu Kyung Jung, Daejeon (KR); Taek Ho Yang, Daejeon (KR); Si Jae Park, Daejeon (KR); Tae Wan Kim, Daejeon (KR)

(73) Assignees: LG CHEM, LTD., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 336 days.

(21) Appl. No.: 13/001,001

(22) PCT Filed: Jun. 24, 2009

(86) PCT No.: PCT/KR2009/003389
§ 371 (c)(1),
(2), (4) Date: Apr. 4, 2011

(87) PCT Pub. No.: WO2009/157702
PCT Pub. Date: Dec. 30, 2009

(65) Prior Publication Data
US 2011/0201067 A1  Aug. 18, 2011

(30) Foreign Application Priority Data
Jun. 24, 2008  (KR) .................. 10-2008-0059779

(51) Int. Cl.
| C12P 7/18 | (2006.01) |
| C12P 7/42 | (2006.01) |
| C12N 1/20 | (2006.01) |
| C12N 15/74 | (2006.01) |
| C07H 21/04 | (2006.01) |
| C08G 63/06 | (2006.01) |
| C12P 7/62 | (2006.01) |
| C12P 21/02 | (2006.01) |

(52) U.S. Cl.
CPC ............... *C08G 63/06* (2013.01); *C12P 7/625* (2013.01); *C12P 21/02* (2013.01)

(58) Field of Classification Search
CPC ............ C12N 2533/40; C12N 9/1029; C12N 15/8243; C12N 9/93; C12N 2501/70; C12N 9/10; C12P 7/625; C12P 7/62; C12P 7/18; C12P 7/56; C12P 7/04
See application file for complete search history.

(56) References Cited

U.S. PATENT DOCUMENTS

2007/0277268 A1   11/2007  Cho et al.

FOREIGN PATENT DOCUMENTS

| JP | 6-510425 A | 11/1994 |
| WO | 2005/033324 A1 | 4/2005 |
| WO | 2006126796 A1 | 11/2006 |
| WO | WO 2006-126796 A1 | 11/2006 |
| WO | WO 2008-062995 A1 | 5/2008 |
| WO | WO 2008-062996 A1 | 5/2008 |
| WO | WO 2008-062999 A1 | 5/2008 |

OTHER PUBLICATIONS

Taguchi et al. A microbial factory for lactate-based polyesters using a lactate-polymerizing enzyme, PNAS (2008), 105: 17323-17327, epub 10/312008.*
Satoh et al. Enzyme-catalyzed poly(3-hydroxybutyrate)synthesis from acetate with CoA recycling and NADPH regeneration in vitro, J of Bioscience and Bioengineering (2003), 95(4): 335-341.*
Dien et al. Fermentation of sugar mixtures using *Escherichia coli* catabolite repression mutants engineered for production of L-lactic acid, J Industrial-Microbiology & Biotechnology (2002), 29: 221-227.*
Yun et al. Enhancement of lactate and succinate formation in adhE or pta-ackA mutant of NADH dehydrogenase-deficient *Escherichia coli*, J Appl Microbiol (2005), 99: 1404-1412.*
Thorsten Selmer et al., Propionate CoA-Transferase from Clostridium propionicum, European Journal of Biochemistry, vol. 2691(1), pp. 372-380 (Jan. 2002).
Chang et al, Homofermentative Production of D- or L-Lactate in Metobolically Engineered *Escherichia coli* RR1, applied and Environmental Microbiology, Apr. 1999, p. 1384-1389, vol. 65, No. 4.
Jung et al, Metabolic Engineering of *Escherichia coli* for the Production of Polylactic Acid and Its Copolymers, Biotechnology and Bioengineering, Jan. 1, 2010, p. 161-171, vol. 105, No. 1.
Yang et al, Redistribution of Metabolic Fluxes in *Escherichia coli* with Fermentative Lactate Dehydrogenase Overexpression and Deletion, Metabolic Engineering, 1999, p. 141-152, vol. 1.
Zhou et al, Production of Optically Pure D-Lactic Acid in Mineral Salts Medium by Metabolically Engineered *Escherichia coli* W3110, Applied and Environmental Microbiology, Jan. 2003, 9.399-407, vol. 69, No. 1.
Zhu et al, Effect of a Single-Gene Knockout on the Metabolic Regulation in *Escherichia coli* for D-Lactate Production Under Microaerobic Condition, Metabolic Engineering, 2005, p. 104-115, vol. 7.
IUBMB Enzyme Nomenclature, EC 2.8.3.1 (1961), http://www.chem.qmul.ac.uk/iubmb/enzymne/EC2/8/3/1.html.

* cited by examiner

*Primary Examiner* — Iqbal H Chowdhury
(74) *Attorney, Agent, or Firm* — Dentons US LLP

(57) ABSTRACT

Provided is a method of preparing polylactate (PLA) or a copolymer thereof using a mutant microorganism in which a gene participating in a coenzyme A (CoA) donor- and lactate-producing pathway is genetically manipulated to increase the productivity of a CoA donor and lactate. Amounts of the CoA donor and the lactate are simultaneously increased in a microbial metabolic pathway to enable effective biosynthesis of PLA and a hydroxyalkanoate-lactate copolymer having a high content of lactate, which is industrially useful.

10 Claims, 1 Drawing Sheet

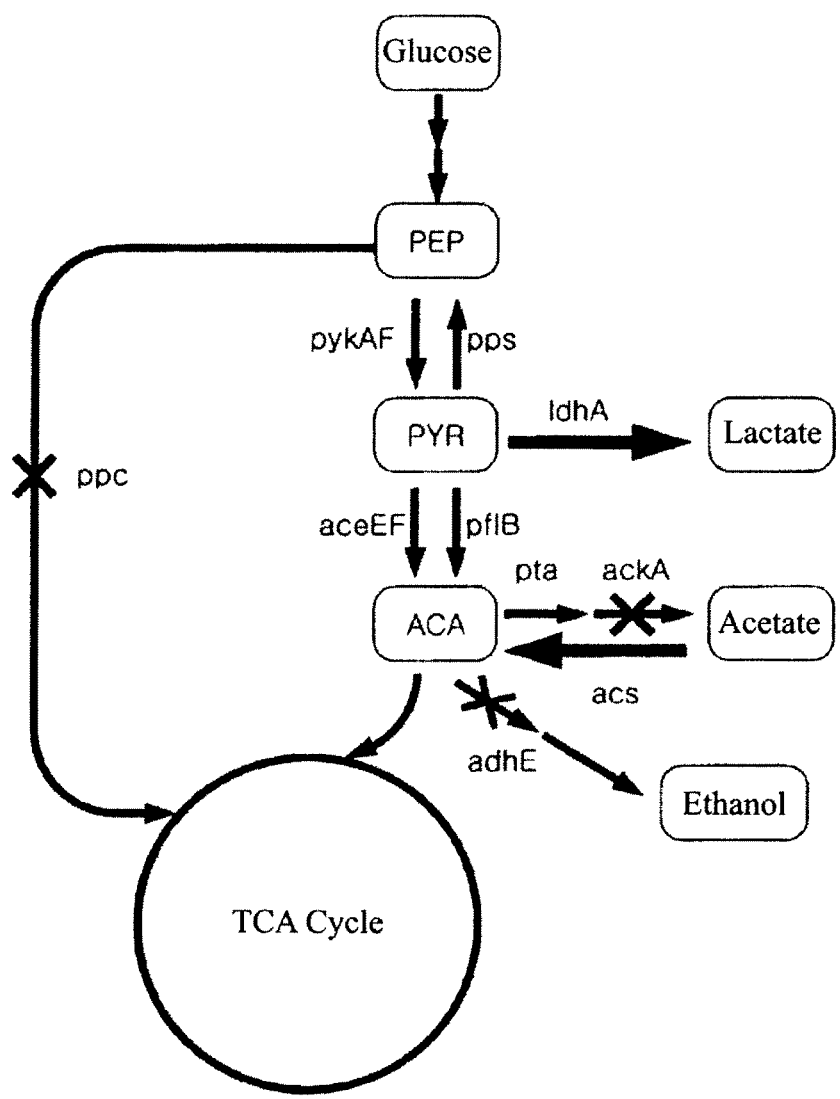

SEQUENCE LISTING

<160> NUMBER OF SEQ ID NOS: 60

<210> SEQ ID NO 1

-continued

```
<211> LENGTH: 71
<212> TYPE: DNA
<213> ORGANISM: Artificial Sequence
<220> FEATURE:
<223> OTHER INFORMATION: FDackA1 primer

<400> SEQUENCE: 1
atttgccatc atcgatgcag taaatggtga agagtacctt tctggtttag taggtgacac    60
tatagaacgc g                                                        71

<210> SEQ ID NO 2
<211> LENGTH: 70
<212> TYPE: DNA
<213> ORGANISM: Artificial Sequence
<220> FEATURE:
<223> OTHER INFORMATION: FDackA2 primer

<400> SEQUENCE: 2
atgtcgagta agttagtact ggttctgaac tgcggtagtt cttcactgaa atttgccatc    60
atcgatgcag                                                          70

<210> SEQ ID NO 3
<211> LENGTH: 70
<212> TYPE: DNA
<213> ORGANISM: Artificial Sequence
<220> FEATURE:
<223> OTHER INFORMATION: RDackA1 primer

<400> SEQUENCE: 3
accgatgtat ttcgccaggc ggtggcagta acgtccatt gcgcgcttcg tagtggatct    60
gatgggtacc                                                          70

<210> SEQ ID NO 4
<211> LENGTH: 71
<212> TYPE: DNA
<213> ORGANISM: Artificial Sequence
<220> FEATURE:
<223> OTHER INFORMATION: RDackA2 primer

<400> SEQUENCE: 4
accagtgaat acaacagcgt ccagacgacc atccatcagc gcagtgtagg caccgatgta    60
tttcgccagg c                                                        71

<210> SEQ ID NO 5
<211> LENGTH: 25
<212> TYPE: DNA
<213> ORGANISM: Artificial Sequence
<220> FEATURE:
<223> OTHER INFORMATION: CupKOackA primer

<400> SEQUENCE: 5
tgtgcaaatt cacaactcag cggga                                         25

<210> SEQ ID NO 6
<211> LENGTH: 25
<212> TYPE: DNA
<213> ORGANISM: Artificial Sequence
<220> FEATURE:
<223> OTHER INFORMATION: CdoKOackA primer

<400> SEQUENCE: 6
tggttccggt agggatcagc ataat                                         25
```

-continued

```
<210> SEQ ID NO 7
<211> LENGTH: 71
<212> TYPE: DNA
<213> ORGANISM: Artificial Sequence
<220> FEATURE:
<223> OTHER INFORMATION: FDppc1 primer

<400> SEQUENCE: 7
atttccataa gttacgctta tttaaagcgt cgtgaattta atgacgtaaa taggtgacac    60
tatagaacgc g                                                        71

<210> SEQ ID NO 8
<211> LENGTH: 70
<212> TYPE: DNA
<213> ORGANISM: Artificial Sequence
<220> FEATURE:
<223> OTHER INFORMATION: FDppc2 primer

<400> SEQUENCE: 8
gcatcttatc cgacctacac ctttggtgtt acttggggcg attttttaac atttccataa    60
gttacgctta                                                          70

<210> SEQ ID NO 9
<211> LENGTH: 70
<212> TYPE: DNA
<213> ORGANISM: Artificial Sequence
<220> FEATURE:
<223> OTHER INFORMATION: RDppc1 primer

<400> SEQUENCE: 9
agcacgaggg tttgcagaag aggaagatta gccggtatta cgcatacctg tagtggatct    60
gatgggtacc                                                          70

<210> SEQ ID NO 10
<211> LENGTH: 70
<212> TYPE: DNA
<213> ORGANISM: Artificial Sequence
<220> FEATURE:
<223> OTHER INFORMATION: RDppc2 primer

<400> SEQUENCE: 10
tgaaaacgag ggtgttagaa cagaagtatt tcagaaaacc ctcgcgcaaa agcacgaggg    60
tttgcagaag                                                          70

<210> SEQ ID NO 11
<211> LENGTH: 22
<212> TYPE: DNA
<213> ORGANISM: Artificial Sequence
<220> FEATURE:
<223> OTHER INFORMATION: Cupppc primer

<400> SEQUENCE: 11
cgcatcttat ccgacctaca cc                                            22

<210> SEQ ID NO 12
<211> LENGTH: 21
<212> TYPE: DNA
<213> ORGANISM: Artificial Sequence
<220> FEATURE:
<223> OTHER INFORMATION: Cdoppc primer

<400> SEQUENCE: 12
cacgagggtt tgcagaagag g                                             21
```

<210> SEQ ID NO 13
<211> LENGTH: 71
<212> TYPE: DNA
<213> ORGANISM: Artificial Sequence
<220> FEATURE:
<223> OTHER INFORMATION: FDadhE1 primer

<400> SEQUENCE: 13
tcgagcagat gatttactaa aaaagtttaa cattatcagg agagcattat taggtgacac    60
tatagaacgc g                                                        71

<210> SEQ ID NO 14
<211> LENGTH: 70
<212> TYPE: DNA
<213> ORGANISM: Artificial Sequence
<220> FEATURE:
<223> OTHER INFORMATION: FDadhE2 primer

<400> SEQUENCE: 14
gattttcata ggttaagcaa atcatcaccg cactgactat actctcgtat tcgagcagat    60
gatttactaa                                                          70

<210> SEQ ID NO 15
<211> LENGTH: 70
<212> TYPE: DNA
<213> ORGANISM: Artificial Sequence
<220> FEATURE:
<223> OTHER INFORMATION: RDadhE1 primer

<400> SEQUENCE: 15
tgatcggcat tgcccagaag gggccgttta tgttgccaga cagcgctact tagtggatct    60
gatgggtacc                                                          70

<210> SEQ ID NO 16
<211> LENGTH: 70
<212> TYPE: DNA
<213> ORGANISM: Artificial Sequence
<220> FEATURE:
<223> OTHER INFORMATION: RDadhE2 primer

<400> SEQUENCE: 16
ggaagccgtt atagtgcctc agtttaagga tcggtcaact aatccttaac tgatcggcat    60
tgcccagaag                                                          70

<210> SEQ ID NO 17
<211> LENGTH: 29
<212> TYPE: DNA
<213> ORGANISM: Artificial Sequence
<220> FEATURE:
<223> OTHER INFORMATION: CupKOadhE primer

<400> SEQUENCE: 17
gatttggatc acgtaatcag tacccagaa                                     29

<210> SEQ ID NO 18
<211> LENGTH: 26
<212> TYPE: DNA
<213> ORGANISM: Artificial Sequence
<220> FEATURE:
<223> OTHER INFORMATION: CdoKOadhE primer

<400> SEQUENCE: 18
ggaaggtgtt ctgcaaatag ttgtgc                                        26

```
<210> SEQ ID NO 19
<211> LENGTH: 61
<212> TYPE: DNA
<213> ORGANISM: Artificial Sequence
<220> FEATURE:
<223> OTHER INFORMATION: FPacs1 primer

<400> SEQUENCE: 19 gccctatgt gtaacaaata accacactgt gaatgttgtc taggtgacac tatagaacgc    60
g                                                                  61

<210> SEQ ID NO 20
<211> LENGTH: 60
<212> TYPE: DNA
<213> ORGANISM: Artificial Sequence
<220> FEATURE:
<223> OTHER INFORMATION: FPacs2 primer

<400> SEQUENCE: 20
tcacgacagt aaccgcacct acactgtcat gacattgctc gccctatgt gtaacaaata    60

<210> SEQ ID NO 21
<211> LENGTH: 60
<212> TYPE: DNA
<213> ORGANISM: Artificial Sequence
<220> FEATURE:
<223> OTHER INFORMATION: FPacs3 primer

<400> SEQUENCE: 21
cgaattgcgc cattgttgca atggcggttt ttattgtttt tcacgacagt aaccgcacct    60

<210> SEQ ID NO 22
<211> LENGTH: 77
<212> TYPE: DNA
<213> ORGANISM: Artificial Sequence
<220> FEATURE:
<223> OTHER INFORMATION: RPacs1 primer

<400> SEQUENCE: 22
tgttatccgc tcacaattcc acacattata cgagccggat gattaattgt caacagctag    60
tggatctgat gggtacc                                                 77

<210> SEQ ID NO 23
<211> LENGTH: 81
<212> TYPE: DNA
<213> ORGANISM: Artificial Sequence
<220> FEATURE:
<223> OTHER INFORMATION: RPacs2 primer

<400> SEQUENCE: 23
cgatgttggc aggaatggtg tgtttgtgaa tttggctcat ggtctgtttc ctgtgtgaaa    60
ttgttatccg ctcacaattc c                                            81

<210> SEQ ID NO 24
<211> LENGTH: 70
<212> TYPE: DNA
<213> ORGANISM: Artificial Sequence
<220> FEATURE:
<223> OTHER INFORMATION: RPacs3 primer

<400> SEQUENCE: 24
ttgttgatac atcgcctcgt actgctgagg gtttatcagg caacggtctg cgatgttggc    60
```
aggaatggtg                                                          70

<210> SEQ ID NO 25
<211> LENGTH: 20
<212> TYPE: DNA
<213> ORGANISM: Artificial Sequence
<220> FEATURE:
<223> OTHER INFORMATION: CUPacs primer

<400> SEQUENCE: 25
agctgaagat acggcgtgcg                                               20

<210> SEQ ID NO 26
<211> LENGTH: 20
<212> TYPE: DNA
<213> ORGANISM: Artificial Sequence
<220> FEATURE:
<223> OTHER INFORMATION: CDOacs primer

<400> SEQUENCE: 26
tcgccccaga aggtatcagg                                               20

<210> SEQ ID NO 27
<211> LENGTH: 60
<212> TYPE: DNA
<213> ORGANISM: Artificial Sequence
<220> FEATURE:
<223> OTHER INFORMATION: FPldhA1 primer

<400> SEQUENCE: 27
catctaatgc aatacgtgtc ccgagcggta gccagatgct aggtgacact atagaacgcg   60

<210> SEQ ID NO 28
<211> LENGTH: 62
<212> TYPE: DNA
<213> ORGANISM: Artificial Sequence
<220> FEATURE:
<223> OTHER INFORMATION: FPldhA2 primer

<400> SEQUENCE: 28
gatcgggaat gattaaacct ttacgcgtaa tgcgtgggct ttcatctaat gcaatacgtg   60
tc                                                                  62

<210> SEQ ID NO 29
<211> LENGTH: 60
<212> TYPE: DNA
<213> ORGANISM: Artificial Sequence
<220> FEATURE:
<223> OTHER INFORMATION: FPldhA3 primer

<400> SEQUENCE: 29
ggtgatatgc gcaagctgac aatctcccac cagataacgg agatcgggaa tgattaaacc   60

<210> SEQ ID NO 30
<211> LENGTH: 77
<212> TYPE: DNA
<213> ORGANISM: Artificial Sequence
<220> FEATURE:
<223> OTHER INFORMATION: RPldhA1 primer

<400> SEQUENCE: 30
tgttatccgc tcacaattcc acacattata cgagccggat gattaattgt caacagctag   60
tggatctgat gggtacc                                                  77

```
<210> SEQ ID NO 31
<211> LENGTH: 81
<212> TYPE: DNA
<213> ORGANISM: Artificial Sequence
<220> FEATURE:
<223> OTHER INFORMATION: RPldhA2 primer

<400> SEQUENCE: 31
tcttgtcgta ctgttttgtg ctataaacgg cgagtttcat ggtctgtttc ctgtgtgaaa    60
ttgttatccg ctcacaattc c                                              81

<210> SEQ ID NO 32
<211> LENGTH: 71
<212> TYPE: DNA
<213> ORGANISM: Artificial Sequence
<220> FEATURE:
<223> OTHER INFORMATION: RPldhA3 primer

<400> SEQUENCE: 32
caaaaaattc cagctcaaag ccaaaggact cgttcacctg ttgcaggtac ttcttgtcgt    60
actgttttgt g                                                         71

<210> SEQ ID NO 33
<211> LENGTH: 27
<212> TYPE: DNA
<213> ORGANISM: Artificial Sequence
<220> FEATURE:
<223> OTHER INFORMATION: CupldhA primer

<400> SEQUENCE: 33
aagcagaatc aagttctacc gtgccga                                        27

<210> SEQ ID NO 34
<211> LENGTH: 25
<212> TYPE: DNA
<213> ORGANISM: Artificial Sequence
<220> FEATURE:
<223> OTHER INFORMATION: CdoldhA primer

<400> SEQUENCE: 34
agccattggc agttttagcg gtttt                                          25

<210> SEQ ID NO 35
<211> LENGTH: 35
<212> TYPE: DNA
<213> ORGANISM: Artificial Sequence
<220> FEATURE:
<223> OTHER INFORMATION: forward primer for phaC1Ps6-19

<400> SEQUENCE: 35
gagagacaat caaatcatga gtaacaagag taacg                               35

<210> SEQ ID NO 36
<211> LENGTH: 33
<212> TYPE: DNA
<213> ORGANISM: Artificial Sequence
<220> FEATURE:
<223> OTHER INFORMATION: reverse primer for phaC1Ps6-19

<400> SEQUENCE: 36
cactcatgca agcgtcaccg ttcgtgcacg tac                                 33

<210> SEQ ID NO 37
<211> LENGTH: 20
<212> TYPE: DNA
```

<213> ORGANISM: Artificial Sequence
<220> FEATURE:
<223> OTHER INFORMATION: primer for addition of BstBI/SbfI recognition site

<400> SEQUENCE: 37
atgcccggag ccggttcgaa                                                 20

<210> SEQ ID NO 38
<211> LENGTH: 35
<212> TYPE: DNA
<213> ORGANISM: Artificial Sequence
<220> FEATURE:
<223> OTHER INFORMATION: primer for addition of BstBI/SbfI recognition site

<400> SEQUENCE: 38
cgttactctt gttactcatg atttgattgt ctctc                                35

<210> SEQ ID NO 39
<211> LENGTH: 35
<212> TYPE: DNA
<213> ORGANISM: Artificial Sequence
<220> FEATURE:
<223> OTHER INFORMATION: primer for addition of BstBI/SbfI recognition site

<400> SEQUENCE: 39
gagagacaat caaatcatga gtaacaagag taacg                                35

<210> SEQ ID NO 40
<211> LENGTH: 33
<212> TYPE: DNA
<213> ORGANISM: Artificial Sequence
<220> FEATURE:
<223> OTHER INFORMATION: primer for addition of BstBI/SbfI recognition site

<400> SEQUENCE: 40
cactcatgca agcgtcaccg ttcgtgcacg tac                                  33

<210> SEQ ID NO 41
<211> LENGTH: 33
<212> TYPE: DNA
<213> ORGANISM: Artificial Sequence
<220> FEATURE:
<223> OTHER INFORMATION: primer for addition of BstBI/SbfI recognition site

<400> SEQUENCE: 41
gtacgtgcac gaacggtgac gcttgcatga gtg                                  33

<210> SEQ ID NO 42
<211> LENGTH: 20
<212> TYPE: DNA
<213> ORGANISM: Artificial Sequence
<220> FEATURE:
<223> OTHER INFORMATION: primer for addition of BstBI/SbfI recognition site

<400> SEQUENCE: 42
aacgggaggg aacctgcagg                                                 20

<210> SEQ ID NO 43
<211> LENGTH: 33
<212> TYPE: DNA
<213> ORGANISM: Artificial Sequence

```
<220> FEATURE:
<223> OTHER INFORMATION: forward primer for S325T substitution

<400> SEQUENCE: 43
ctgaccttgc tggtgaccgt gcttgatacc acc                                    33

<210> SEQ ID NO 44
<211> LENGTH: 33
<212> TYPE: DNA
<213> ORGANISM: Artificial Sequence
<220> FEATURE:
<223> OTHER INFORMATION: reverse primer for S325T substitution

<400> SEQUENCE: 44
ggtggtatca agcacggtca ccagcaaggt cag                                    33

<210> SEQ ID NO 45
<211> LENGTH: 36
<212> TYPE: DNA
<213> ORGANISM: Artificial Sequence
<220> FEATURE:
<223> OTHER INFORMATION: forward primer for Q481M substitution

<400> SEQUENCE: 45
cgagcagcgg gcatatcatg agcatcctga acccgc                                 36

<210> SEQ ID NO 46
<211> LENGTH: 36
<212> TYPE: DNA
<213> ORGANISM: Artificial Sequence
<220> FEATURE:
<223> OTHER INFORMATION: reverse primer for for Q481M substitution

<400> SEQUENCE: 46
gcgggttcag gatgctcatg atatgcccgc tgctcg                                 36

<210> SEQ ID NO 47
<211> LENGTH: 33
<212> TYPE: DNA
<213> ORGANISM: Artificial Sequence
<220> FEATURE:
<223> OTHER INFORMATION: forward primer for E130D substitution

<400> SEQUENCE: 47
atcaacctca tgaccgatgc gatggcgccg acc                                    33

<210> SEQ ID NO 48
<211> LENGTH: 33
<212> TYPE: DNA
<213> ORGANISM: Artificial Sequence
<220> FEATURE:
<223> OTHER INFORMATION: reverse primer for E130D substitution

<400> SEQUENCE: 48
ggtcggcgcc atcgcatcgg tcatgaggtt gat                                    33

<210> SEQ ID NO 49
<211> LENGTH: 39
<212> TYPE: DNA
<213> ORGANISM: Artificial Sequence
<220> FEATURE:
<223> OTHER INFORMATION: forward primer for amplification of cp-pct

<400> SEQUENCE: 49
ggaattcatg agaaaggttc ccattattac cgcagatga                              39
```

-continued

```
<210> SEQ ID NO 50
<211> LENGTH: 46
<212> TYPE: DNA
<213> ORGANISM: Artificial Sequence
<220> FEATURE:
<223> OTHER INFORMATION: reverse primer for amplification of cp-pct

<400> SEQUENCE: 50
gctctagatt aggacttcat ttccttcaga cccattaagc cttctg          46

<210> SEQ ID NO 51
<211> LENGTH: 32
<212> TYPE: DNA
<213> ORGANISM: Artificial Sequence
<220> FEATURE:
<223> OTHER INFORMATION: forward primer for addition of SbfI/NdeI
      recognition site

<400> SEQUENCE: 51
aggcctgcag gcggataaca atttcacaca gg                          32

<210> SEQ ID NO 52
<211> LENGTH: 31
<212> TYPE: DNA
<213> ORGANISM: Artificial Sequence
<220> FEATURE:
<223> OTHER INFORMATION: reverse primer for addition of SbfI/NdeI
      recognition site

<400> SEQUENCE: 52
gcccatatgt ctagattagg acttcatttc c                           31

<210> SEQ ID NO 53
<211> LENGTH: 18
<212> TYPE: DNA
<213> ORGANISM: Artificial Sequence
<220> FEATURE:
<223> OTHER INFORMATION: forward primer for random mutation

<400> SEQUENCE: 53
cgccggcagg cctgcagg                                          18

<210> SEQ ID NO 54
<211> LENGTH: 20
<212> TYPE: DNA
<213> ORGANISM: Artificial Sequence
<220> FEATURE:
<223> OTHER INFORMATION: reverse primer for random mutation

<400> SEQUENCE: 54
ggcaggtcag cccatatgtc                                        20

<210> SEQ ID NO 55
<211> LENGTH: 27
<212> TYPE: DNA
<213> ORGANISM: Artificial Sequence
<220> FEATURE:
<223> OTHER INFORMATION: forward primer for phaC1Ps6-19400 having
      E130D, S325T, S477R, and Q481M mutation

<400> SEQUENCE: 55
ttcgtgctgt cgagcagagg gcatatc                                27

<210> SEQ ID NO 56
<211> LENGTH: 27
<212> TYPE: DNA
```

```
<213> ORGANISM: Artificial Sequence
<220> FEATURE:
<223> OTHER INFORMATION: reverse primer for phaC1Ps6-19400 having E130D,
      S325T, S477R, and Q481M mutation

<400> SEQUENCE: 56
gatatgccct ctgctcgaca gcacgaa                                           27

<210> SEQ ID NO 57
<211> LENGTH: 30
<212> TYPE: DNA
<213> ORGANISM: Artificial Sequence
<220> FEATURE:
<223> OTHER INFORMATION: forward primer for phaC1Ps6-19400 having E130D,
      S477F, and Q481K mutation

<400> SEQUENCE: 57
gaattcgtgc tgtcgagctt tgggcatatc                                        30

<210> SEQ ID NO 58
<211> LENGTH: 30
<212> TYPE: DNA
<213> ORGANISM: Artificial Sequence
<220> FEATURE:
<223> OTHER INFORMATION: reverse primer for phaC1Ps6-19400 having E130D,
      S477F, and Q481K mutation

<400> SEQUENCE: 58
gatatgccca aagctcgaca gcacgaattc                                        30

<210> SEQ ID NO 59
<211> LENGTH: 28
<212> TYPE: DNA
<213> ORGANISM: Artificial Sequence
<220> FEATURE:
<223> OTHER INFORMATION: forward primer for phaC1Ps6-19400 having E130D,
      S477F, and Q481K mutation

<400> SEQUENCE: 59
gggcatatca aaagcatcct gaacccgc                                          28

<210> SEQ ID NO 60
<211> LENGTH: 28
<212> TYPE: DNA
<213> ORGANISM: Artificial Sequence
<220> FEATURE:
<223> OTHER INFORMATION: reverse primer for phaC1Ps6-19400 having E130D,
      S477F, and Q481K mutation

<400> SEQUENCE: 60
gcgggttcag gatgcttttg atatgccc                                          28
```

METHOD FOR PREPARING POLYLACTATE AND COPOLYMER THEREOF USING A MUTANT MICROORGANISM WITH ENHANCED POLYLACTATE, AND THE COPOLYMER PRODUCING CAPABILITY THEREOF

This application is a National Stage Entry of International Application No. PCT/KR2009/003389, filed Jun. 24, 2009, and claims the benefit of Korean Application No. 10-2008-0059779, filed on Jun. 24, 2008, which is hereby incorporated by reference for all purposes as if fully set forth herein.

TECHNICAL FIELD

The present invention relates to a method of preparing polylactate and a copolymer thereof using a mutant microorganism having enhanced capability to produce the polylactate and the copolymer thereof.

BACKGROUND ART

Polylactate (PLA) is a typical biodegradable polymer derived from lactate, and is highly applicable in general-purpose or medical polymers. In recent years, PLA has been synthesized by polymerizing lactates produced by microbial fermentation, but this direct polymerization of lactates can produce only PLA having a low molecular weight (1000 to 5000 daltons). In order to synthesize PLA of 100,000 daltons or more, low molecular weight PLAs obtained by the direct polymerization of lactates may be polymerized into higher molecular weight PLAs using a chain coupling agent. However, this method of preparing a higher molecular weight PLA has problems in that its processes are complicated due to addition of a solvent or a chain coupling agent, and removing the solvent or chain coupling agent is difficult as well. The method of producing high molecular weight PLA widely used in recent years includes converting lactate into lactide, and subjecting a ring of the lactide to a ring-opening condensation reaction to synthesize PLAs.

Meanwhile, polyhydroxyalkanoate (PHA) is polyester which is accumulated in a microorganism as an energy or carbon source storage material when there are excessive carbon sources but a lack of other nutrients such as phosphorus, nitrogen, magnesium and oxygen. The PHA is known as an alternative for conventional synthetic plastics since it has similar properties to conventional synthetic polymers derived from petroleum and shows perfect biodegradability.

In order to produce PHA from a microorganism, an enzyme converting metabolic products of the microorganism into a PHA monomer and a PHA synthase synthesizing a PHA polymer using the PHA monomer are essentially required.

The PHA synthase synthesizes PHA using hydroxyacyl-CoA as a substrate. However, there are no cases where PLA and a copolymer thereof are naturally produced or produced in recombinant cells or plants since hydroalkanoate, such as lactate hydroxylated at the carbon-2 position, is not suitable for substrate specificity of PHA synthase. In order to provide lactyl-CoA, the inventors can successfully synthesize PLA and a PLA copolymer using a *Clostridium propionicum*-derived propionyl-CoA transferase and a polyhydroxyalkanoate synthase of *Pseudomonas* sp. 6-19 using the lactyl-CoA as a substrate (Korean Patent Application No. 10-2005-0043798).

However, the conventional developed microorganisms still have low capability to produce PLA and a PLA copolymer, and thus development of a microorganism having improved capability to produce the PLA and PLA copolymer is required.

DISCLOSURE

Technical Problem

Therefore, an object of the present invention is to provide a method of effectively preparing polylactate (PLA) or copolymers thereof using a mutant microorganism effectively producing the PLA or copolymers thereof.

Technical Solution

One aspect of the present invention provides a method of preparing polylactate (PLA) or copolymers thereof using a mutant microorganism in which at least one gene participating in a coenzyme A (CoA) donor- and lactate-producing pathway is genetically manipulated to increase the productivity of a CoA donor and lactate.

Advantageous Effects

According to the present invention, amounts of the coenzyme A donor and the lactate are simultaneously increased in a microbial metabolic pathway to enable effective biosynthesis of polylactate (PLA) and a hydroxyalkanoate-lactate copolymer having high content of lactate, which is industrially useful.

DESCRIPTION OF DRAWINGS

These and other features, aspects, and advantages of preferred embodiments of the present invention will be more fully described in the following detailed description, taken accompanying drawing. In the drawing:

FIG. 1 shows an endogenous metabolic pathway of a mutant microorganism in which an ackA, adhE, acs, ppc or ldhA gene is inactivated or amplified to enhance the productivity of polylactate (PLA) and a copolymer thereof.

BEST MODE

Production of lactyl CoA that is a polylactate (PLA) monomer should be increased to effectively synthesize PLA or a copolymer thereof. For this purpose, a metabolic flux within a microorganism should be changed to increase an amount of a CoA donor required for biosynthesis of lactyl CoA and increase an amount of a major precursor substrate, lactate, as well. Biosynthesis efficiency of the lactyl CoA is not highly improved even by the increase in amount of the CoA donor or the lactate. Therefore, the present invention is intended to increase amounts of the CoA donor and the lactate at the same time in the microbial metabolic pathway, thereby increasing biosynthesis efficiency of the PLA or a copolymer thereof and increasing a content of lactate in a polymer.

For the supply of lactate, a method of supplying lactate from the outside of cells to introduce lactate into the cells by means of a lactate transporter and a method of using intracellular lactate generated from glucose in an anaerobic condition are provided. When lactate is supplied from the outside of the cells, the uptake of the lactate may be restricted. Also, the lactate supplied from the outside of the cells is transferred into the cells while being converted into pyruvate by D-lactate dehydrogenase and L-lactate dehydrogenase present in a cell membrane of *Escherichia coli*. This is not compatible with the objects of the present invention to increase the productivity of lactyl CoA. Therefore, the present invention is intended to select a pathway of generating lactate using glucose and synthesizing the lactyl-CoA from the lactate, and then genetically manipulate a microbial metabolic pathway so as to increase the production of lactyl CoA.

For this purpose, the present invention aims to provide a method of preparing PLA or a hydroxyalkanoate-lactate copolymer. Here, the method includes preparing a mutant microorganism in which at least one gene participating in a CoA donor- and lactate-producing pathway is genetically manipulated to increase the production of a CoA donor and lactate; incubating the mutant microorganism in a medium containing glucose or glucose and hydroxyalkanoate; and recovering PLA or a hydroxyalkanoate-lactate copolymer from the mutant microorganism.

According to one embodiment of the present invention, the CoA donor may be acetyl CoA. For the CoA donor, the acetyl CoA may highly become a coenzyme donor in the microbial metabolic pathway in which glucose is used to synthesize lactate.

In order to increase an amount of the acetyl CoA that is one of the CoA donors, a gene coding for an enzyme participating in an acetate-producing pathway in a microorganism or a gene coding for an enzyme participating in an ethanol-producing pathway may be inactivated, or a gene coding for an enzyme re-converting acetate into acetyl CoA may be amplified. An amount of the acetyl CoA may also be further increased by inactivating or amplifying at least two of the genes.

In order to produce lactyl CoA, in addition to the acetyl CoA, the coenzyme A donor that is able to provide the coenzyme A may include β-ketoadipyl-CoA, γ-butyrobetanyl-CoA, (R)-methylmalonyl-CoA, (S)-methyl-malonyl-CoA, 2'-(5"-phosphoribosyl)-3'-dephospho-CoA, 2'-(5"-triphosphoribosyl)-3'-dephospho-CoA, 3,4-dihydroxyphenylacetyl-CoA, 3-hydroxyadipyl-CoA, 3-hydroxybutyryl-CoA, 3-hydroxyphenylacetyl-CoA, 3-methylcrotonyl-CoA, 4-hydroxyphenylacetyl-CoA, cis-dihydrodiol derivatives of phenylacetyl-CoA, Δ2-enoyl-CoA, 2-trans-4-cis-dienoyl-CoA, 3-hydroxyacyl-CoA, 3-ketoacyl-CoA, cis-2-enoyl-CoA, cis-3-enoyl-CoA, trans-2-enoyl-CoA, trans-3-enoyl-CoA, cis-2,3-dehydroacyl-CoA, D-3-dihydroxyacyl-CoA, fatty acyl CoA, long-chain acyl-CoA, trans,trans-Δ2-Δ4-dienoyl-CoA, very long chain fatty acyl-CoA, CoA derivatives, acetoacetyl-CoA, acetyl-CoA, ω-carboxyacyl-CoA, acyl-CoA, L-3-hydroxyacyl-CoA, butyryl-CoA, coenzyme A (CoA), a coenzyme-A-group (CoA), coumaroyl-CoA, crotonobetainyl-CoA, crotonyl-CoA, D-carnitinyl-CoA, dephospho-CoA, formyl-CoA, isovaleryl-CoA, L-carnitinyl-CoA, malonyl-CoA, O-succinylbenzoyl-CoA, oxalyl-CoA, palmitoyl CoA, phenylacetyl-CoA, pimeloyl-CoA, propionyl-CoA, succinyl-CoA, trans-Δ2,cis-Δ4-decadienoyl-CoA, trans-Δ2-decenoyl-CoA, lactyl CoA, etc. When the CoA other than the acetyl CoA is used as the CoA donor, a kind of the inactivated or amplified genes may be changed to increase an amount of these coenzyme A donors.

In order to increase an amount of lactate in a metabolic flux in a microorganism, a gene coding for an enzyme participating in a phosphoenolpyruvate-consuming reaction in the microorganism may be inactivated, or a gene coding for an enzyme participating in conversion of pyruvate into lactate may be amplified as well. An amount of the lactate may also be further increased by inactivating or amplifying at least two of the genes. In order to employ intracellular lactate generally generated from glucose in an anaerobic condition, cells are first sufficiently incubated in an aerobic condition to grow the cells, and the aerobic condition should be changed into an anaerobic condition or a microanaerobic condition to generate lactate. However, when the gene is manipulated to increase an amount of the lactate as described above, an effective production system in which both the cell growth and the production of a polymer using intracellular lactate are realized through a one-step culture may be constructed.

In the present invention, any microorganism that can synthesize PLA or a copolymer thereof may be used. Such a microorganism may include a bacterium, a yeast, a mold, etc. For example, the bacterium may include the genera *Alcaligenes, Pseudomonas, Escherichia, Ralstonia, Bacillus, Corynebacterium*, etc., but the present invention is not particularly limited thereto. According to one embodiment of the present invention, the bacterium may be *Escherichia coli* (*E. coli*). According to one embodiment of the present invention, a mutant *E. coli* prepared by genetically manipulating *E. coli* XL1-Blue is disclosed, but the present invention is not particularly limited thereto.

According to one embodiment of the present invention, an enzyme participating in the acetate-producing pathway may be, for example, acetate kinase, and a gene coding for the enzyme may be ackA.

According to one embodiment of the present invention, an enzyme participating in the major ethanol-producing pathway may be, for example, acetaldehyde dehydrogenase, and a gene coding for the enzyme may be adhE.

According to one embodiment of the present invention, an enzyme re-converting the acetate into acetyl CoA may be, for example, acetyl CoA synthetase, and a gene coding for the enzyme may be acs.

According to one embodiment of the present invention, an enzyme participating in the phosphoenolpyruvate-consuming reaction may be, for example, phosphoenolpyruvate carboxylase, and a gene coding for the enzyme may be ppc.

According to one embodiment of the present invention, an enzyme participating in the conversion of the pyruvate into lactate may be, for example, lactate dehydrogenase, and a gene coding for the enzyme may be ldhA.

According to another embodiment of the present invention, in the mutant microorganism, both the gene coding for the enzyme participating in the acetate-producing pathway and the gene coding for the enzyme participating in the phosphoenolpyruvate-consuming reaction may be inactivated, and the gene coding for the enzyme participating in the conversion of the pyruvate into lactate may be amplified.

According to still another embodiment of the present invention, in the mutant microorganism, the gene coding for the enzyme participating in the acetate-producing pathway may be inactivated and the gene coding for the enzyme re-converting the acetate into acetyl CoA may be amplified, and at the same time the gene coding for the enzyme participating in the phosphoenolpyruvate-consuming reaction may be inactivated and the gene coding for the enzyme participating in the conversion of the pyruvate into lactate may be amplified.

In the present invention, the term "inactivate or inactivating" refers to preventing transcription of a gene due to mutation or preventing translation of the transcribed mRNA into an intact protein. In order to "inactivate" a gene, the gene may be mutated by deleting some of the gene or modifying a nucleotide sequence of the gene.

In the present invention, the term "amplify or amplifying" refers to a process in which an expression level of a gene is higher than an endogenous expression level of the gene. When no genes to be amplified are present in a microorganism before mutation of the microorganism, at least one of the genes may be introduced and amplified in the microorganism. When at least one gene to be amplified is present in a microorganism before mutation of the microorganism, at least one gene may be further introduced into the microorganism in the same manner, or a preexisting gene may be genetically manipulated to increase an expression level of the gene. For example, when a gene whose expression is amplified is present in a microorganism to be mutated, the expression of the gene may be amplified by substituting a strong promoter for a native promoter serving to induce the expression of the gene. Therefore, the amplification of the gene may be induced by the substitution of the native promoter with the strong promoter according to one embodiment of the present invention. Examples of such a strong promoter include a trc promoter, a tac promoter, a T7 promoter, a lac promoter, etc.

The mutant microorganism may be further manipulated to increase amount of pyruvate. Pyruvate is a common precursor of lactate and acetyl CoA that is one of the CoA donors. When the amount of pyruvate is increased, the acetyl coenzyme A and the lactate are increased in amount. Therefore, according to still another embodiment of the present invention, the mutant microorganism may be a microorganism in which at least one of the following genes may be further attenuated or inactivated to increase the amount of the pyruvate: aceE, aceF, lpdA, pfkA, pfkB, tpiA, sdhA, sdhB, sdhC, sdhD, fumA, fumB, fumC, eptB, gpmA, gpmB, ptsG, mdh, ppc, pgi, glgC, sucA, sucB, ribA, folE, pflB, etc. For example, when genes, aceE, aceF and lpdA, coding for pyruvate dehydrogenase converting pyruvate into acetyl CoA, or a gene, pflB, coding for pyruvate formate liase converting pyruvate into formate is attenuated or inactivated, amounts of acetyl CoA and lactate are increased with an increase of the pyruvate. Also, a metabolic flux from malate to pyruvate may be enhanced by attenuating or inactivating a gene, mdh, coding for malate dehydrogenase converting malate into oxaloacetate. Alternatively, the metabolic flux to pyruvate may be enhanced by attenuating or inactivating a gene, ptsG, coding for one member of a phosphotransferase enzyme family serving to take up glucose while consuming a precursor, phosphoenolpyruvate, of the pyruvate, or a gene, tpiA, coding for triose phosphate isomerase converting glyceraldehyde 3-phosphate into dihydroxyacetone phosphate during a glycolytic pathway in which glucose is converted into pyruvate.

When the mutant microorganism is incubated in a glucose-containing medium, PLA may be obtained from the microorganism. Also, when the mutant microorganism is incubated in a medium containing glucose and hydroxyalkanoate, a hydroxyalkanoate-lactate copolymer may be obtained from the microorganism. A kind of the hydroxyalkanoate-lactate copolymer may be varied according to the kind of the hydroxyalkanoate included in the medium.

According to one embodiment of the present invention, the hydroxyalkanoate may include at least one selected from the group consisting of 3-hydroxybutyrate, 3-hydroxyvalerate, 4-hydroxybutyrate, medium-chain length (D)-3-hydroxycarboxylic acid having 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvalerate, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methyl ester, 3-hydroxyadipinic acid-methyl ester, 3-hydroxysuberic acid-methyl ester, 3-hydroxyazelaic acid-methyl ester, 3-hydroxysebacic acid-methyl ester, 3-hydroxysuberic acid-ethyl ester, 3-hydroxysebacic acid-ethyl ester, 3-hydroxypimelic acid-propyl ester, 3-hydroxysebacic acid-benzil ester, 3-hydroxy-8-acetoxyoctanoic acid, 3-hydroxy-9-acetoxynonanoic acid, phenoxy-3-hydroxybutyrate, phenoxy-3-hydroxyvalerate, phenoxy-3-hydroxyheptanoic acid, phenoxy-3-hydroxyoctanoic acid, para-cyanophenoxy-3-hydroxybutyrate, para-cyanophenoxy-3-hydroxyvalerate, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethyl-5-heptenoic acid.

Mode for Invention

One embodiment of the present invention discloses a method of effectively producing poly(D-lactate) and poly(3-hydroxybutyrate-co-D-lactate) having a high content of lactate by genetically manipulating *E. coli* XL1-Blue. According to the method of the present invention, it is possible to prepare various kinds of poly(hydroxyalkanoate-lactate).

Hereinafter, the advantages and characteristics of the present invention and a method for achieving the advantages and characteristics will now be described in more detail referring to the following examples. However, the description proposed herein is just a preferable example for the purpose of illustrations only, not intended to limit the scope of the invention, so it should be understood that other equivalents and modifications could be made thereto without departing from the spirit and scope of the invention. Therefore, the examples of the present invention are provided to complete the disclosure of the present invention and completely inform a person having an ordinary skill in the art to which the present invention pertains of the scope of the present invention, and thus the present invention is merely defined by the scope of the appended claims.

Example 1

Preparation of Mutant Microorganism that Effectively Produces PLA and 3-Hydroxybutyrate-Lactate Copolymer A mutant *E. coli* that effectively produces PLA or a copolymer thereof was prepared from *E. coli* XL1-Blue in this Example 1 by inactivating a gene, ackA, coding for an enzyme participating in an acetate-producing pathway or a gene, adhE, coding for an enzyme participating in an ethanol-producing pathway or amplifying a gene, acs, coding for an enzyme re-converting acetate into acetyl coenzyme A (CoA), and simultaneously inactivating a gene, ppc, coding for an enzyme participating in a phosphoenolpyruvate-consuming reaction or amplifying a gene, ldhA, coding for an enzyme participating in conversion of pyruvate into lactate, and transforming the mutant *E. coli* with a recombinant vector containing a PHA synthase gene and a propionyl-CoA-transferase gene. FIG. 1 shows an endogenous metabolic pathway of a mutant microorganism in which an ackA, adhE, acs, ppc or ldhA gene is inactivated or amplified to enhance the productivity of PLA and a copolymer thereof.

Example 1-1

Preparation of Mutant Microorganism Having Increased Amounts of Acetyl-CoA and Lactate 1-1-1: Deletion of ackA, adhE or ppc Gene An ackA, adhE or ppc gene was deleted from *E. coli* XL1-Blue (Stratagene) by a one-step inactivation method (Warner et al., PNAS, 6; 97(12):6640-6645, 2000) using the following primers.

For deletion of the ackA gene, a pMlocX vector [Lee, K. H., Park, J. H., Kim, T. Y., Kim, H. U. & Lee, S. Y. Systems metabolic engineering of *Escherichia coli* for L-threonine production. Molecular systems biology 3, 149(2007)] was used as a template, and a pair of primers SEQ ID NOS: 1 and 3 were used to conduct primary PCR. Then, the resulting DNA fragment was used as template, and a pair of primers SEQ ID NOS: 2 and 4 were used to conduct secondary primer-extension PCR. The DNA fragment obtained in the secondary PCR was electroporated into competent cells (electroporation-competent cells) of XL1-Blue in which λ-red recombinase was expressed and XL1-Blue-derived mutant strains to prepare an ackA gene-deleted mutant strain. In order to confirm the deletion of the ackA gene, colony PCR was conducted using a pair of primers SEQ ID NOS: 5 and 6.

For deletion of the ppc gene, pairs of primers SEQ ID NOS: 7 and 9 and SEQ ID NOS: 8 and 10, were sequentially used in the same manner. In order to confirm the deletion of the ppc gene, a pair of primers SEQ ID NO: 11 and 12 were used.

For deletion of the adhE gene, pairs of primers SEQ ID NOS: 13 and 15 and SEQ ID NOS: 14 and 16 were also sequentially used in the same manner. In order to confirm the deletion of the adhE gene, a pair of primers SEQ ID NOS: 17 and 18 were used.

1-1-2: Amplification of acs or ldhA Gene acs and ldhA genes were amplified in the same manner as described in Example 1-1-1 by substituting native promoters of the acs and ldhA genes on *E. coli* chromosomal DNA with a trc promoter that is one of strong promoters, respectively, using a one-step inactivation method (Warner et al., PNAS, 6; 97(12):6640-6645, 2000).

In order to substitute the native promoter of the acs gene with the trc promoter, a pMloxC vector was used as a template to conduct primary PCR using a pair of primers SEQ ID NOS: 19 and 22. Then, the resulting DNA fragment was used as a template to conduct secondary PCR using a pair of primers SEQ ID NOS: 20 and 23. The DNA fragment obtained in the secondary PCR was used as a template to conduct tertiary PCR using a pair of primers SEQ ID NOS: 21 and 24, thereby obtaining a final DNA fragment. Then, the final DNA fragment was electroporated into competent cells (electroporation-competent cells) of XL1-Blue in which λ-red recombinase was expressed and XL1-Blue-derived mutant strains to prepare a mutant strain in which the native promoter of the acs gene was substituted with the trc promoter. In order to confirm the substitution of the promoter of the acs gene, colony PCR was conducted using a pair of primers SEQ ID NOS: 25 and 26.

In order to substitute the native promoter of the ldhA gene with the trc promoter, pairs of primers SEQ ID NOS: 27 and 30, SEQ ID NOS: 28 and 31, and SEQ ID NOS: 29 and 32 were also sequentially used, and a pair of primers SEQ ID NOS: 33 and 34 were used to confirm the substitution.

1-1-3: Preparation of Mutant Microorganism whose ackA, adhE, acs, ppc or ldhA Gene is Inactivated or Amplified A mutant microorganism JLX1-9 in which various combinations of the ackA, adhE, acs, ppc and ldhA genes were inactivated or amplified was prepared in the same manner as in Example 1-1-1 or 1-1-2.

The *E. coli* XL1-Blue-derived mutant strains prepared in the method and their chromosomal DNA characteristics are listed in the following Table 1.

TABLE 1

| Mutant Strains | Chromosomal DNA Characteristics |
| --- | --- |
| JLX1 | XB Δ ackA |
| JLX2 | XB ptrc-ldhA |
| JLX3 | XB Δ ppc |
| JLX4 | XB Δ ackA ptrc-ldhA |
| JLX5 | XB ptrc-ldhA Δ ppc |
| JLX6 | XB Δ ackA Δ ppc |
| JLX7 | XB Δ ackA ptrc-ldhA Δ ppc |
| JLX8 | XB Δ ackA ptrc-ldhA Δ ppc ptrc-acs |
| JLX9 | XB Δ ackA ptrc-ldhA Δ ppc ptrc-acs Δ adhE |

Example 1-2

Construction of Recombinant Vector Containing PHA Synthase and Propionyl-CoA-Transferase Genes 1-2-1. Construction of pPs619C1300-CPPCT Recombinant Vector In order to isolate a PHA synthase (phaC1$_{Ps6-19}$) gene derived from *Pseudomonas* sp. 6-19 (KCTC 11027BP), the total DNA of *Pseudomonas* sp. 6-19 was extracted, a pair of primers having base sequences of SEQ ID NOS: 35 and 36 were constructed based on a sequence of the phaC1$_{Ps6-19}$ gene (AeJin, SONG, Master's Thesis, Department of Chemical and Biomolecular Engineering, KAIST, 2004), and PCR was conducted to obtain a phaC1$_{Ps6-19}$ gene. PCR products were electrophoresized on an agarose gel to confirm the presence of a gene fragment having a size of 1.7 kbp, which corresponds to the phaC1$_{Ps6-19}$ gene.

An operon-type constitutive expression system in which a monomer-supplying enzyme and synthase are expressed together was introduced to induce expression of the phaC1$_{Ps6-19}$ synthase.

A DNA fragment containing a *Ralstonia eutropha* H16-derived PHB-producing operon was digested with BamHI/EcoRI from a pSYL105 vector (Lee et al., Biotech. Bioeng., 1994, 44:1337-1347), and inserted into a BamHI/EcoRI recognition site of pBluescript II (Stratagene) to construct a pReCAB recombinant vector.

It is widely known that a pReCAB vector constitutively expresses PHA synthase (phaC$_{RE}$) and monomer-supplying enzymes (phaA$_{RE}$ & phaB$_{RE}$) by a PHB operon promoter, and works well in *E. coli* (Lee et al., Biotech. Bioeng., 1994, 44:1337-1347). The pReCAB vector was digested with BstBI/SbfI to remove the PHA synthase (phaC$_{RE}$) of *R. eutropha* H16. Then, the phaC1$_{Ps6-19}$ gene obtained above was inserted into a BstBI/SbfI recognition site to prepare a pPs619C1-ReAB recombinant vector.

In order to prepare a fragment of the phaC1$_{Ps6-19}$ synthase gene having both ends corresponding respectively to the BstBI/SbfI recognition sites, an endogenous BstBI site was first removed without a change in amino acids using a site directed mutagenesis (SDM) method, and primers having base sequences of SEQ ID NOS: 37 and 38, SEQ ID NOS: 39 and 40, SEQ ID NO: 41 and SEQ ID NO: 42 were used to conduct overlapping PCR so as to add a BstBI/SbfI recognition site.

In order to confirm the PHB synthesis of the phaC1$_{Ps6-19}$ synthase, *E. coli* XL-1Blue (Stratagene) was transformed with the pPs619C1-ReAB recombinant vector, and grown in a PHB detection medium (a Luria Bertani (LB) agar, 20 g/L glucose, 0.5 μg/ml Nile red). As a result, the PHB synthesis was not observed.

Three domains of amino acids affecting short chain length (SCL) activities were found through amino acid sequence analysis, and phaC1$_{Ps6-19}$ synthase variants as listed in the following Table 2 were prepared using an SDM method using pairs of primers SEQ ID NOS: 43 to 48.

TABLE 2

| Recombinant Vector | Nucleotide Substitution | Amino Acid Substitution | Primers |
|---|---|---|---|
| pPs619C1200-ReAB | AGC →ACC | S325T | SEQ ID NOS: 43/44 |
| | CAG →ATG | Q481M | SEQ ID NOS: 45/46 |
| pPs619C1300-ReAB | GAA →GAT | E130D | SEQ ID NOS: 47/48 |
| | AGC →ACC | S325T | SEQ ID NOS: 43/44 |
| | CAG →ATG | Q481M | SEQ ID NOS: 45/46 |

*E. coli* XL-1Blue was transformed with these recombinant vectors, and grown in a PHB detection medium (an LB agar, 20 g/L glucose, 0.5 μg/ml Nile red). As a result, it was confirmed that PHB was produced in both of the *E. coli* XL-1 Blue transformed with the pPs619C1200-ReAB and the *E. coli* XL-1Blue transformed with the pPs619C1300-ReAB.

That is, 3HB-CoA was produced from glucose by the monomer-supplying enzymes, phaA$_{RE}$ and phaB$_{RE}$, and SCL variants (phaC1$_{Ps6-19}$200 & phaC1$_{Ps6-19}$300) of the phaC1$_{Ps6-19}$ synthase synthesized PHB using the 3HB-CoA as a substrate.

In order to construct an operon-type constitutive expression system in which propionyl-CoA transferase is expressed together to provide a monomer, lactyl-CoA, required for synthesis of PLA and a PLA copolymer, *Clostridium propionicum*-derived propionyl-CoA transferase (CP-PCT) was used.

A fragment obtained by subjecting chromosomal DNA of *C. propionicum* to PCR using primers SEQ ID NOS: 49 and 50 was used as cp-pct. In this case, an NdeI site originally present in wild-type CP-PCT was removed using an SDM method for the ease of cloning. For addition of a SbfI/NdeI recognition site, primers having base sequences of SEQ ID NOS: 51 and 52 were also used to conduct overlapping PCR.

The pPs619C1300-ReAB vector containing an SCL mutant of the phaC1$_{Ps6-19}$ synthase, phaC1$_{Ps6-19}$300, was digested with SbfI/NdeI to remove the *R. eutrophus* H16-derived monomer-supplying enzymes (phaA$_{RE}$ & phaB$_{RE}$), and the PCR-cloned CP-PCT gene was then inserted into the SbfI/NdeI recognition site to prepare a pPs619C1300-CP-PCT recombinant vector.

1-2-2. Construction of pPs619C1300-CPPCT532 Recombinant Vector

It is known that, when CP-PCT is over-expressed in *E. coli*, it causes severe metabolic disorders, thereby causing toxicity. All the recombinant *E. coli* died with addition of an inducer in an IPTG-induced expression system using a tac promoter or a T7 promoter widely used for expression of a recombinant protein.

Therefore, development of a mutant of the *C. propionicum* propionate CoA transferase that can effectively provide lactyl-CoA is required.

For this purpose, a constitutive expression system in which lactyl-CoA is weakly expressed but constitutively expressed with growth of a microorganism was used to synthesize a lactate polymer and a lactate copolymer.

In order to introduce a random mutation into cp-pct, the pPs619C1300-CPPCT prepared in Example 1-2-1 was used as a template, and a pair of primers SEQ ID NOS: 53 and 54 were used to conduct error-prone PCR in a condition where Mn$^{2+}$ is supplemented and there is a difference in concentrations of dNTPs.

Then, in order to amplify a PCR fragment including random mutation, PCR was conducted in a common condition using the pair of primers SEQ ID NOS: 53 and 54.

The pPs619C1300-CPPCT vector containing phaC1$_{Ps6-19}$300, which is an SCL mutant of phaC1$_{Ps6-19}$ synthase, was digested with SbfI/NdeI to remove wild-type cp-pct, and a ligation mixture in which the amplified variant PCR fragment was inserted into an SbfI/NdeI recognition site was prepared, and introduced into *E. coli* JM109 to prepare a CP-PCT library with a scale of approximately 10$^5$. The prepared CP-PCT library was grown for 3 days in a polymer detection medium (an LB agar, 20 g/L glucose, 1 g/L 3HB, 0.5 μg/ml Nile red), and then screened to confirm whether a polymer was generated, thereby primarily selecting approximately 80 candidates. The candidates were grown for 4 days in a liquid medium (an LB agar, 20 g/L glucose, 1 g/L 3HB, 100 mg/L ampicillin, 37° C.) under a polymer generation condition, and analyzed using fluorescence-activated cell sorting (FACS), thereby selecting two final samples.

A gene sequence analysis was conducted to locate mutations of the prepared CP-PCT variants. The results are listed in the following Table 3.

TABLE 3

| Recombinant Vector | Nucleotide Substitution |
|---|---|
| CP-PCT Variant 512 | A1200G |
| CP-PCT Variant 522 | T78C, T669C, A1125G, T1158C |

Random mutation was conducted again in the Error-prone PCR method using the finally screened variants (CP-PCT Variant 512, CP-PCT Variant 522), thereby obtaining CP-PCT variants 531-536 as listed in the following Table 4.

TABLE 4

| Recombinant Vector | Mutations | Silent Mutations |
|---|---|---|
| CP-PCT Variant 531 | Gly335Asp | A1200G |
| CP-PCT Variant 532 | Ala243Thr | A1200G |
| CP-PCT Variant 533 | Asp65Gly | T669C, A1125G, T1158C |
| CP-PCT Variant 534 | Asp257Asn | A1200G |
| CP-PCT Variant 535 | Asp65Asn | T669C, A1125G, T1158C |
| CP-PCT Variant 536 | Thr199Ile | T669C, A1125G, T1158C |

Then, in order to amplify a PCR fragment containing CpPct532 mutation, the primers of SEQ ID NO: 53 and 54 were used to conduct PCR under a common condition. The pPs619C1300-CPPCT vector was digested with SbfI/NdeI to remove a CPPCT portion, and a ligation mixture in which the amplified CpPct532 PCR fragment was inserted into a SbfI/NdeI recognition site was prepared to prepare a pPs619C1300-CPPCT532 vector.

1-2-3. Preparation of pPs619C1400-CPPCT532 (p400-532) Recombinant Vector

When PLA and a PLA copolymer are synthesized using PHA synthase that does not effectively use lactyl-CoA, their synthesis efficiency is very low. Therefore, use of PHA synthase that can effectively use lactyl-CoA is very important in synthesis of the PLA and the PLA copolymer. Accordingly, the inventors have found a system capable of preparing a lactate polymer and a lactate copolymer in high efficiency using a variant of the polyhydroxyalkanoate synthase in the Pseudomonas sp. 6-19 and using lactyl-CoA as a substrate.

A Pseudomonas sp. 6-19-derived PHA synthase variant (phaC1$_{Ps6-19}$400) having an amino acid sequence mutated at E130D, S325T, S477R and Q481M was prepared, based on the phaC1$_{Ps6-19}$ synthase variant (phaC1$_{Ps6-19}$300) prepared in Example 1-2-1, using an SDM method using a pair of primers: SEQ ID NOS: 55 and 56.

E. coli JM109 was transformed with a recombinant vector (pPs619C1400-CPPCT532) obtained using the resutling variant, and grown in a polymer detection medium (an LB agar, 20 g/L glucose, 2 g/L 3HB, 0.5 μg/ml Nile red) supplemented with 3HB. As a result, the production of the polymer was confirmed.

1-2-4. Preparation of pPs619C1310-CPPCT532 (p310-532) Recombinant Vector

When PLA and a PLA copolymer are synthesized using PHA synthase that does not effectively use lactyl-CoA, their synthesis efficiency is very low. Therefore, use of PHA synthase that can effectively use lactyl-CoA is very important in synthesis of the PLA and the PLA copolymer. Therefore, a Pseudomonas sp. 6-19-derived PHA synthase variant (phaC1$_{Ps6-19}$310) having an amino acid sequence mutated at E130D, S477F and Q481K was prepared, based on the phaC1$_{Ps6-19}$ synthase variant (phaC1$_{Ps6-19}$300) prepared in Example 1-2-1, using an SDM method using pairs of primers SEQ ID NOS: 57, 58, 59 and 60.

E. coli JM109 was transformed with a recombinant vector (pPs619C1310-CPPCT532) obtained using the resulting variant, and grown in a polymer detection medium (an LB agar, 20 g/L glucose, 2 g/L 3HB, 0.5 μg/ml Nile red) supplemented with 3HB. As a result, the production of the polymer was confirmed.

1-3. Preparation of Mutant Microorganism that Effectively Produces PLA and 3-Hydroxybutyrate-Lactate Copolymer A mutant microorganism that effectively produces PLA and poly(3-hydroxybutyrate-co-lactate) was prepared by introducing the pPs619C1400-CPPCT532 or the pPs619C1310-CPPCT532 vector prepared in Examples 1-2-3 and 1-2-4 into the mutant microorganism in which the amounts of the acetyl-CoA and the lactate were increased as prepared in Example 1-1.

The mutant microorganism was screened on an LB plate medium supplemented with 10 μg/ml tetracycline, 100 μg/ml ampicillin and 20 g/L glucose. The transformed strain was inoculated in 10 ml of an LB medium, and pre-incubated at 30° C. for 12 hours. Then, 1 ml of the pre-culture solution was inoculated with 10 μg/ml tetracycline, 100 μg/ml ampicillin and 10 μg/ml thiamine into a 250 ml flask containing 100 ml of a medium prepared by mixing 20 g of glucose, 6.67 g of KH$_2$PO$_4$, 4 g of (NH$_4$)$_2$HPO$_4$, 0.8 g of citric acid, 0.8 g of MgSO$_4$.7H$_2$O, and 5 ml of a trace metal solution (including 10 g of FeSO$_4$.7H$_2$O, 1.35 g of CaCl$_2$, 2.25 g of ZnSO$_4$.7H$_2$O, 0.5 g of MnSO$_4$.4H$_2$O, 1 g of CuSO$_4$.5H$_2$O, 0.106 g of (NH$_4$)$_6$Mo$_7$O$_{24}$.4H$_2$O, 0.23 g of Na$_2$B$_4$O$_7$.10H$_2$O, 10 ml of 35% HCl per 1 L of distilled water) per 1 L of distilled water, pH of the medium being adjusted to 7.0 using 10N NaOH. Then, the resulting mixture was incubated at 30° C. for 72 to 96 hours at 200 rpm. In this case, 2 g/L of DL-3-hydroxybutyrate sodium salt (ACROS) was fed once or twice at the beginning of culturing to produce a poly(3-hydroxybutyrate-co-lactate) copolymer. 4 g/L of succinate was supplemented to incubate a strain whose cells were hardly grown due to deletion of the ppc gene among the mutated strains. Also, 1 mM IPTG was supplemented at OD600 of approximately 0.5 to express the ldhA and acs genes whose promoters were substituted with the trc promoter.

When the incubation was completed, a culture solution was centrifuged to recover a pallet. The recovered pallet was washed three times with distilled water, and dried at 100° C. for 24 hours in an oven. Then, some of the dried pallet was taken, and subjected to a gas chromatography (GC) assay to measure a content of P(3HB-co-LA) synthesized in the cells. Reference materials used in this assay were a P(3HB-co-3HV) copolymer (a content of 3HV in the copolymer accounts for a weight ratio of approximately 12%) and a PLA homopolymer. Approximately 3 to 10 wt % of a PLA homopolymer can be generated by the metabolic manipulations, production of the P(3HB-co-LA) copolymer showed excellently improved effects such as an increase of an LA fraction in a polymer of 1.7 to 4.3 times and an increase in content of the polymer of 1.4 to 27.3 times.

Example 2

Comparison of Productivity of Polymer According to Culture Volume Condition in Mutant Microorganism that Effectively Produces PLA and 3-Hydroxybutyrate-Lactate Copolymer In order to determine an effect of a culture condition and thus a lactate production level on cell growth of a microorganism and generation of P(3HB-co-LA), the microorganism was incubated in different culture volumes. For this purpose, an XB/p400-532 strain was incubated in 250 ml flasks containing 50 ml, 100 ml and 150 ml of media, respectively. The XB/p400-532 strain was a strain into which the pPs619C1400-CPPCT532 vector was introduced without manipulating the metabolic flux of E. coli XL1-Blue.

The results of the production of the polymer according to the culture volume conditions in the XB/p400-532 strain are listed in the following Table 5.

TABLE 5

| Culture Volume (ml) | Generated Polymer |
|---|---|
| 50 | P(3HB-co-19.86 mol % LA) 24.46 wt % |
| 100 | P(3HB-co-39.43 mol % LA) 34.43 wt % |
| 150 | P(3HB-co-43.85 mol % LA) 36.93 wt % |

As a medium volume increased, the cell growth was relatively slowed with formation of a (micro)anaerobic condition as it was expected, and a content of the polymer increased approximately 1.5 times. Also a lactate (LA) fraction in the polymer increased 2.2 times as production of lactate increased under the (micro)anaerobic condition.

In order to determine an effect of a JLX7/p400-532 of the present invention which was metabolically manipulated based on the above-mentioned facts, a flask culture was conducted in culture volumes of 50 ml and 100 ml.

The results of the production of the polymer according to the culture volume conditions in the XB/p400-532 strain and the mutant microorganism JLX7/p400-532 of the present invention are listed in the following Table 6.

TABLE 6

| Culture Volume | Polymer-Producing Strains and Production Results | |
|---|---|---|
| (ml) | XB/p400-532 | JLX7/p400-532 |
| 50 | P(3HB-co-14.32 mol % LA) 26.72 wt % | P(3HB-co-49.55 mol % LA) 33.06 wt % |
| 100 | P(3HB-co-40.45 mol % LA) 34.93 wt % | P(3HB-co-63.95 mol % LA) 56.73 wt % |

When the mutant microorganism JLX7/p400-532 was incubated in a culture volume of 50 ml, a content of P(3HB-co-LA) was increased 1.24 times, compared to when the XB/p400-532 was used as a host strain, and a concentration of the polymer was also increased 1.98 times. In addition, an LA fraction in the polymer was increased from 14.32 mol % to 49.55 mol % (approximately 3.46 times). When the mutant microorganism JLX7/p400-532 was incubated in a culture volume of 100 ml, a content of P(3HB-co-LA) was increased 1.62 times, compared to when the XB/p400-532 was used as the host strain, and a concentration of the polymer was also increased 2.98 times. In addition, the LA fraction in the polymer was increased from 40.45 mol % to 63.95 mol % (1.58 times).

An increase and control of the LA fraction is the key to improve a strain as much as the LA fraction in the PLA copolymer having an important effect on physical properties of the polymer.

The LA fraction was increased from 14.32 mol % to 49.55 mol % (approximately 3.46 times) when the mutant microorganism JLX7/p400-532 was incubated in a culture volume of 50 ml, whereas, when the mutant microorganism JLX7/p400-532 was incubated in a culture volume of 1000 ml, an increase in the LA fraction was relatively low, that is, the LA fraction was increased from 40.45 mol % to 63.95 mol % (1.58 times), but had the highest absolute value (63.95 mol %). That is, an increase in the LA fraction was relatively high in the 50 ml culture, but had a highest value of approximately 50 mol %, which does not exceed the highest value (63.95 mol %) in the 100 ml culture. This indicates that the culture condition in addition to metabolic engineering at a gene level is a regulatory factor that should be optimized to produce PLA and a copolymer thereof.

Example 3

Comparison of Productivity of Polymer in Mutant Microorganism According to Combinations of Mutant Genes An effect of a combination of genetic mutations applied to the mutant microorganism of the present invention on an increase in productivity of the polymer was confirmed.

As described above, 20 g/L glucose was added as a carbon source to an MR medium used as a base medium, and 10 μg/ml tetracycline, 100 μg/ml ampicillin and 10 μg/ml thiamine were added as markers. Also, 2 g/L of DL-3-hydroxybutyrate sodium salt (ACROS) was fed once (M20 in the case of a p310-532 vector) or twice (M18 in the case of a p400-532 vector) at the beginning of culture, and incubated at 30° C. for 72 hours at 200 rpm.

When the XB and JLX1 strains were used as the host strains, they were incubated under the above-mentioned condition without addition of additional items, and when the JLX3, JLX5, JLX6, JLX7 and JLX8 strains were used, 4 g/L succinate was further fed at the beginning of culture so as to relieve inhibition of cell growth by deletion of the ppc gene. When the JLX2, JLX4, JLX5, JLX7 and JLX8 strains were used, 1 mM IPTG was added at $OD_{600}$ of approximately 0.5 to induce expression of a ptrc-ldhA gene or ptrc-ldhA and ptrc-acs genes.

The productivities of the polymers in the mutant microorganisms, in which the XB wild-type strain and the JLX1, JLX2, JLX3, JLX4, JLX5, JLX6 and JLX7 strains listed in Table 1 were used as the host strain and the p400-532 vector was introduced into each strain, are listed in the following Table 7.

TABLE 7

| Host Strains | Polymer-Producing Results |
|---|---|
| XB Wild Type | P(3HB-co-40.44 mol % LA) 34.73 wt % |
| JLX1 | P(3HB-co-37.34 mol % LA) 15.86 wt % |
| JLX2 | P(3HB-co-45.10 mol % LA) 48.82 wt % |
| JLX3 | P(3HB-co-46.85 mol % LA) 52.26 wt % |
| JLX4 | P(3HB-co-44.98 mol % LA) 28.48 wt % |
| JLX5 | P(3HB-co-50.83 mol % LA) 56.14 wt % |
| JLX6 | P(3HB-co-36.89 mol % LA) 45.27 wt % |
| JLX7 | P(3HB-co-63.95 mol % LA) 55.53 wt % |

Also, the productivities of the polymers in the mutant microorganisms, in which the XB wild-type strain and the JLX1, JLX2, JLX3, JLX4, JLX5, JLX6, JLX7 and JLX8 strains listed in Table 1 were used as the host strain and the p310-532 vector was introduced into each strain, are listed in the following Table 8.

TABLE 8

| Host Strains | Polymer-Producing Results |
|---|---|
| XB Wild Type | P(3HB-co-14.39 mol % LA) 1.13 wt % |
| JLX1 | P(3HB-co-26.18 mol % LA) 11.48 wt % |
| JLX2 | P(3HB-co-39.09 mol % LA) 20.74 wt % |
| JLX3 | P(3HB-co-38.76 mol % LA) 6.09 wt % |
| JLX4 | P(3HB-co-35.78 mol % LA) 17.54 wt % |
| JLX5 | P(3HB-co-60.78 mol % LA) 14.11 wt % |

TABLE 8-continued

| Host Strains | Polymer-Producing Results |
|---|---|
| JLX6 | P(3HB-co-39.24 mol % LA) 13.20 wt % |
| JLX7 | P(3HB-co-58.16 mol % LA) 16.16 wt % |
| JLX8 | P(3HB-co-61.52 mol % LA) 30.90 wt % |

The production of the polymer was affected by the activities of all enzymes that directly affect the metabolic flux of the host strain and the production of the polymer. Therefore, as listed in Tables 7 and 8, it was seen that an LA fraction in the produced polymer and a content of the polymer were changed even in the same host cells according to the activities of the used enzymes. Nonetheless, it was revealed that the productivity of the polymer was generally excellent in the case of the JLX5, JLX7 or JLX8 strain.

Example 4

Comparison of Productivity of Polymer According to Amount of Supplied 3-Hydroxybutyrate For biosynthesis of a PLA homopolymer and a P(3HB-co-LA) copolymer having a high content of lactate (LA), the productivities of these polymers were determined by adjusting an amount of supplied 3-hydroxybutyrate(3HB).

When the XB wild-type strain and the JLX7 strain were used as host strains and the p400-532 vector was introduced into each strain, the productivities of the polymers according to the amounts (0, 0.5, 1, 2, 4 and 8 g/L) of the supplied 3HB are listed in the following Table 9.

TABLE 9

| 3-HB Concentration | Polymer-Producing Strains and Production Results | |
|---|---|---|
| (g/L) | XB/p400-532 | JLX7/p400-532 |
| 0 | No Polymer Produced | PLA 10.44 wt % |
| 0.5 | — | P(3HB-co-86.16 mol % LA) 31.35 wt % |
| 1 | — | P(3HB-co-80.73 mol % LA) 41.93 wt % |
| 2 | P(3HB-co-40.45 mol % LA) 34.93 wt % | P(3HB-co-69.13 mol % LA) 49.15 wt % |
| 4 | — | P(3HB-co-61.01 mol % LA) 55.34 wt % |
| 8 | — | P(3HB-co-33.32 mol % LA) 60.76 wt % |

When the XB wild-type strain and the JLX7, JLX8 and JLX9 strains were used as host strains and the p310-532 vector was introduced into each strain, the productivities of the polymers according to the amounts (0, 0.5, 1, 2 and 4 g/L) of the supplied 3HB are listed in the following Table 10.

TABLE 10

| 3-HB Concentration | Polymer-Producing Strains and Production Resutls | | | |
|---|---|---|---|---|
| (g/L) | XB/p310-532 | JLX7/p310-532 | JLX8/p310-532 | JLX9/p310-532 |
| 0 | No Polymer Produced | PLA 3.18 wt % | PLA 3.16 wt % | — |
| 0.5 | No Polymer Produced | P(3HB-co-80.41 mol % LA) 12.87 wt % | P(3HB-co-78.23 mol % LA) 13.97 wt % | P(3HB-co-77.9 mol % LA) 14.43 wt % |
| 1 | P(3HB-co-45.17 mol % LA) 0.23 wt % | P(3HB-co-72.04 mol % LA) 19.43 wt % | P(3HB-co-72.81 mol % LA) 23.55 wt % | P(3HB-co-71.15 mol % LA) 24.06 wt % |
| 2 | P(3HB-co-24 mol % LA) 0.875 wt % | P(3HB-co-60.68 mol % LA) 26.82 wt % | P(3HB-co-59.38 mol % LA) 36.32 wt % | P(3HB-co-62.25 mol % LA) 37.02 wt % |
| 4 | — | — | P(3HB-co-55.4 mol % LA) 64.75 wt % | P(3HB-co-57.06 mol % LA) 60.72 wt % |

When both the p400-532 and p310-532 host cells were the XB wild-type strains, they did not produce the PLA homopolymer and the P(3HB-co-LA) copolymer having an LA content of 50 mol % or more, whereas the JLX 7, JLX8 or JLX9 strains produced 3 to 10 wt % the PLA homopolymer and 13 to 65 wt % the P(3HB-co-LA) copolymer having an LA content of 50 to 86 mol %.

The present invention has been described in detail. However, it should be understood that the detailed description and specific examples, while indicating preferred embodiments of the invention, are given by way of illustration only, since various changes and modifications within the scope of the invention will become apparent to those skilled in the art from this detailed description.

The invention claimed is:

1. A method of preparing polylactate (PLA), comprising:
preparing a mutant microorganism in which a gene coding for an enzyme participating in an acetate-producing pathway is inactivated in the mutant microorganism or a gene coding for an enzyme re-converting acetate into acetyl CoA is amplified by over-expression of a gene to increase the productivity of the CoA donor, and a gene coding for an enzyme participating in conversion of pyruvate into lactate is amplified by over-expression of a gene to increase the productivity of the lactate;
incubating the mutant microorganism in a medium containing glucose or glucose and hydroxyalkanoate; and
recovering PLA from the mutant microorganism,
wherein the enzyme participating in the acetate-producing pathway is acetate kinase A,
wherein the enzyme re-converting the acetate into the acetyl CoA is acetyl-CoA synthetase, and
wherein the enzyme participating in the conversion of the pyruvate into the lactate is lactate dehydrogenase A.

2. The method according to claim 1, wherein the CoA donor is acetyl-CoA.

3. The method according to claim 1, wherein the mutant microorganism is selected from the group consisting of a bacterium, a yeast and a mold.

4. The method according to claim 3, wherein the bacterium is selected from the group consisting of the genera *Alcaligenes*, *Pseudomonas*, *Escherichia*, *Ralstonia*, *Bacillus* and *Corynebacterium*.

5. The method according to claim 3, wherein the bacterium is *Escherichia coli*.

6. The method according to claim 1, wherein, in the mutant microorganism, the gene coding for the enzyme participating in the acetate-producing pathway is inactivated, the gene coding for the enzyme re-converting acetate into acetyl CoA is amplified to increase the productivity of the CoA donor, and the gene coding for the enzyme participating in the conversion of pyruvate into lactate is amplified to increase the productivity of the lactate.

7. The method according to claim 1, wherein the amplification of the genes is performed by substitution of a native promoter with a strong promoter.

8. The method according to claim 7, wherein the strong promoter is selected from the group consisting of a trc promoter, a tac promoter, a T7 promoter and a lac promoter.

9. The method according to claim 1, wherein the mutant microorganism has pflB (pyruvate formate lyase) gene further attenuated or inactivated.

10. The method according to claim 1, wherein the hydroxyalkanoate is 3-hydroxybutyrate.

\* \* \* \* \*